United States Patent [19]

Giraudi

[11] Patent Number: 4,774,225
[45] Date of Patent: Sep. 27, 1988

[54] ODORANTS

[75] Inventor: Edouard Giraudi, La Roquette sur Siagne, France

[73] Assignee: Societe Anonyme Roure Bertrand Dupont, Argenteuil, France

[21] Appl. No.: 114,785

[22] Filed: Oct. 30, 1987

[30] Foreign Application Priority Data

Nov. 3, 1986 [EP] European Pat. Off. ....... 86.810497.7

[51] Int. Cl.⁴ .................... C07D 319/08; A61K 7/46
[52] U.S. Cl. ........................................ 512/9; 549/336; 568/831
[58] Field of Search ............................ 549/336; 512/9

Primary Examiner—Norma S. Milestone
Attorney, Agent, or Firm—Sidney Wallenstein

[57] ABSTRACT

The invention relates to novel odorant substances. These are compounds of the formula

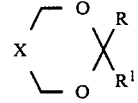

wherein R and $R^1$ are H, $CH_3$, $C_2H_5$, $C_3H_7$ or $CH(CH_3)_2$ and the sum of the carbon atoms in R and $R^1$ does not exceed 6, and X is caran-yliden (2,2) or caran-yliden (4,4).

The invention relates also to the preparation of these novel substances and to odorant compositions containing these substances.

8 Claims, No Drawings

ODORANTS

The invention is concerned with novel odorant substances. These are the compounds of the formula

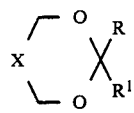

wherein R and R¹ are H, CH₃, C₂H₅, C₃H₇ or CH(CH₃)₂ and the sum of the carbon atoms in R and R¹ does not exceed 6, and X is caran-yliden (2,2) or caran-yliden (4,4).

Formula I encompasses thus the compounds of formulae

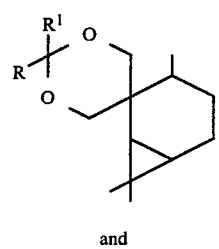

and

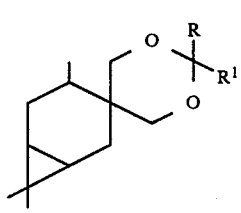

The compounds I have particular organoleptic properties, on the basis of which they are excellently suited as odorant substances.

The invention is accordingly also concerned with the use of the compounds I as odorant substances and odorant substance compositions containing compounds I.

2,2,3',7',7'-pentamethyl-spiro[1,3-dioxane-5,2'-norcaran] is the preferred compound I. Its odor characteristics can be described as follows: amber, woody (of most interesting complexity), recalling the odour of the fruits of eucalyptus in a very early green stage.

Further interesting compounds I are: 2,3',7',7'-tetramethyl-spiro[1,3-dioxane-5,2'-norcaran], 3',7',7'-trimethyl-2-ethyl-spiro[1,3-dioxane-5,2'-norcaran], 2,3',7',7'-tetramethyl-2-ethyl-spiro[1,3-dioxane-5,2'-norcaran], 3',7',7'-trimethyl-2,2-diethyl-spiro[1,3-dioxane-5,2'-norcaran] and 3',7',7'-trimethyl-spiro[1,3-dioxane-5,2'-norcaran].

The invention is also concerned with a process for the manufacture of the compounds I. This process comprises reacting 2- or 4-[bis-(hydroxymethyl)]caran with a carbonyl compound of the general formula

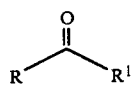

wherein R and R¹ are as above.

The manufacture of the compounds I is conveniently effected using methods described in the literature, such as acid-catalysed acetalisation or ketalisation, or, trans-acetalisation or trans-ketalisation, e.g. by using an acetal or ketal of a low boiling compound II, see e.g.

—Frans A. J. Meskens, Synthesis (1981), 501 seq.
—M. Delmas, A. Gaset, Informations Chimie No. 232, (December 1982), 151–158.

As acidic catalysts there can be used the substances which are usually used for acetalisations or ketalisations; for example, mineral acids such as hydrochloric acid or sulphuric acid, phosphoric acid and perchloric acid, etc., strong organic acids such as trichloroacetic acid or p-toluenesulphonic acid, (PTSOH) etc. and Lewis acids such as, for example, boron trifluoride, etc.

The reaction is suitably effected at room temperature or slightly elevated temperatures, if necessary in the presence of a solvent.

As solvents, there can be used for example, aromatic and saturated aliphatic hydrocarbons (.e.g. benzene, toluene or n-pentane).

As pointed out above, the invention is also concerned with the use of the compounds I as odorant substances.

The dioxanes in accordance with the invention are all distinguished by woody and amber notes, exhibiting, in particular, flowery green side notes. Worth of mentioning are their odorous power and the tenacity. They are either colorless or slightly colored, readily accessible, the individual batches are constant in odor, non-irritant, stable and convenient to handle.

Thus, the novel compounds I are organoleptically totally different from the structurally related dioxane of the formula

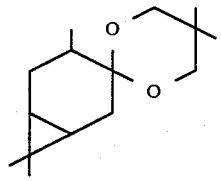

as discussed on the "Colloque sur la chimie des terpènes", in Grasse, France, April 24–25, 1986.

This latter compound can be described as green, herbaceous with balsamous and resinous side notes and which compound did, due to its simple and common organoleptic aspect, not attract the interest of the perfumers at all.

The compounds I combines with numerous known odorant substance ingredients of natural or synthetic origin, whereby the range of the natural raw substances can embrace not only readily volatile but also semi-volatile and difficulty-volatile components, and that of the synthetics can embrace representatives from practically all classes of substances, as is evident from the following compilation:

Natural products, such as tree moss absolute, basil oil, agrumen oils (such as begamot oil, mandarin oil etc.), palmarosa oil, patchouli oil, petitgrain oil, wormwood oil, lavender oil, geranium oil, clove oil alcohols, such as farnesol, geraniol, linalool, nerol, phenylethyl alcohol, rhodinol, cinnamic alcohol, aldehydes, such as citral, Helional ®, α-hexylcinnamaldehyde, hydroxycitronellal, Lilial ® (p-tert. butyl-α-methyl-dihydrocinnamaldehyde), methylnonylacetaldehyde, ketones, such as allylionone, α-ionone, β-ionone, isoraldein (isomethyl-α-ionone), methylionone,
esters, such as allyl phenoxyacetate, benzyl salicylate, cinnamyl propionate, citronellyl acetate, benzyl acetate, citronellyl ethoxalate (citronellyl-.O—CO—CO.OC$_2$H$_5$), decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate,
lactones, such as γ-undecalactone,
various components often used in perfumery, such as musk ketone, indole, methyleugenol, Vertofix ® (acetylated cedarwood oil), Képhalis ® (1-ethoxy-4(1'-ethoxy-vinyl)-3,3,5,5-tetramethyl-cyclohexene/4(1'-ethoxy-vinyl)-3,3,5,5-tetramethyl-cyclohexanone, Argéolène ® (Schiffbase of hydroxcitronellal and methyl anthranilate), etc.

Worthy of note is, further, the manner in which the compounds I rounds-off and harmonizes the olfactory notes of known compositions without, however, dominating in an unpleasant manner. The dioxanes can be used in a great variety of odorant compositions, e.g. in compositions of the following types:
oriental chypre, modern fougère, green tobacco, floral chypre, fresh fougère, floral sweet citrus, woody animal, oriental, floral fruity, floral aldehyde, leather, spicy, green, woody amber, musk, tobacco, etc.

The compounds of formula I (or its mixtures) can be used in wide limits which can extend in compositions, for example, from 0.1 (detergents)–5% (alcoholic solutions). It will be appreciated, however, that these values are not limiting values, as the experienced perfumer can also achieve effects with even lower concentrations or can synthesize novel complexes with even higher amounts. The preferred concentrations range between 0.2 and 2%. The compositions manufactured with I can be used for all kinds of perfumed consumer goods (eau de cologne, eau de toilette, extracts, lotions, creams, shampoos, soaps, salves, powders, toothpastes, mouth washes, deodorants, detergents, tobacco, etc.).

The compounds I can accordingly be used in the manufacture of compositions and, as will be evident from the above compilation, a wide range of known odorant substances or odorant substance mixtures can be used. In the manufacture of such compositions the known odorant substances enumerated above can be used according to methods known to the perfumer, such as e.g. from W. A. Poucher, Perfumes, Cosmetics and Soaps 2, 7th Edition, Chapman and Hall, London 1974.

EXAMPLE 1

(a) 92,8 g of potassium hydroxide and 1,46 l of ethanol (96%) are given into a 3 necked flask, equipped with a refrigerator, a dropping funnel and a thermometer. The outside is cooled with water and there is added within 1 hour at room temperature, 517 g of 30% aqueous formaldehyde. There are now added, within 1 hour, under stirring and at a temperature of 20°–25° C., 275 g (1,65 moles) of 2-formyl-caran. Agitation is continued for 3 hours at room temperature. Neutralisation of the medium is effected by the addition of 95 ml of acetic acid (pH 5–6), the refrigerator is replaced by a Vigreux column followed by a refrigerator, and the alcohol is distilled off at atmospheric pressure. There are obtained 1,55 l of distillate. The reaction product is cooled, taken up in 200 ml of methylene chloride added through the dropping funnel, decanted, the aqueous layer is extracted with 2×100 ml of methylene chloride; the combined organic layers are washed with 2×100 ml of sodium chloride solution, the organic layers are dried using sodium sulfate. The concentration is effected by means of a rotary evaporator, the final pressure is 20 mmHg. There are obtained 256,5 g of crude reaction product. A distillation step leads to 195 g of 2-[bis-(hydroxymethyl)]caran, b.p. 107°–108° C./0,1 mmHg, m.p. 70°–71° C.

(b) 154 g (0,77 moles) of 2-[bis-(hydroxymethyl)]caran, 773 g of acetone and 1,6 g of p-toluene sulfonic acid are given into a 2 l 3 necked flask, equipped with mechanical stirrer, a refrigerator and a thermometer. The mixture is stirred for 2 hours at room temperature. There are now added 16 g of solid sodium carbonate, this addition is followed by a 30 minutes agitation period. A filtration step is followed by distilling off the acetone on a rotary evaporator, the final pressure being 20 mmHg. The 179 g crude material are fractionated at 0,1 mmHg. There are obtained 161 g of 2,2,3',7',7'-pentamethyl-spiro[1,3-dioxane-5,2'-norcaran].

EXAMPLE 2

(a) 39 g of potassium hydroxyde and 530 ml of 96% ethanol are given into a 3 necked flask, equipped with a mechanical stirrer, an ascending refrigerator, a 250 ml dropping funnel and a thermometer. An outside water circulation is effected and there are added, within 30 minutes, 188 g of 30% aqueous formaldehyde. Within 15 minutes, there are added at 20°–25° C. 100 g of 4-formyl-caran. Stirring is maintained for 3 hours at 20°–25° C. 2,8 ml of 90% aqueous acetic acid are added, the alcohol is distilled off, the reaction mass is cooled, the aqueous layer is decanted and washed with methylene chloride. The combined organic phases are washed with sodium chloride solution. The solvent is distilled, finally at a pressure of 20 mmHg. There are obtained 97,2 g of 4-[bis-(hydroxymethyl)]caran, having a melting point of 65°–66° C.

(b) 39,6 g of 4-[bis-(hydroxymethyl)caran, 198 g of acetone and 1 g of p-toluene sulfonic acid are given into a 500 ml flask. There follows stirring for 2 hours at room temperature. Neutralisation of the reaction medium is effected by means of 3 g of sodium carbonate. There follows a filtration step, and distillation of the excess acetone. The crude reaction product is fractionated at a pressure of 0,5 mmHg. There are obtained 38,3 g of 2,2,3',7',7'-pentamethyl-spiro[1,3-dioxane-5,4'-norcaran]; b.p. 75°–76° C./0,5 mmHg.

Further compounds I' were obtained from the relevant compounds II as follows:

TABLE

| R | R$^1$ | catalyst | physical data | odor |
|---|---|---|---|---|
| CH$_3$ | C$_2$H$_5$ | pTSOH, H$_2$O | b.p. = 75,77° C./0,05 mmHg<br>n$_D^{20}$ = 1.4809 | amber, lactone, woody, slightly milky; powerful, tenacious. |
| C$_2$H$_5$ | C$_2$H$_5$ | pTSOH, H$_2$O | b.p. = 91° C./0,01 mmHg<br>n$_D^{20}$ = 1.4852 | amber, woody, milky, slightly flowery; powerful, tenacious. |

TABLE-continued

| R | R$^1$ | catalyst | physical data | odor |
|---|---|---|---|---|
| H | H | H$_2$SO$_4$* | b.p. = 71,74° C./0,1 mmHg<br>n$_D^{20}$ = 1.4879 | amber, woody, slightly lactone, animal side-note; powerful, tenacious. |
| H | C$_2$H$_5$ | HCl conc. | b.p. = 83,87° C./0,2 mmHg<br>n$_D^{20}$ = 1.4795 | amber, woody, agreeable roasted side-note; powerful, tenacious. |

*using the acetal CH$_2$(OEt)$_2$ of the carbonyl compound II

| R | R$^1$ | catalyst | physical data | odor |
|---|---|---|---|---|
| H | C$_3$H$_7$ | HCl conc. | b.p. = 95–100° C./0,1 mmHg<br>n$_D^{20}$ = 1.4778 | woody, green flowery, amber note developing on evaporation; powerful, tenacious. |
| H | CH$_3$ | HCl gaseous or H$_2$SO$_4$* | b.p. = 80° C./0,6 mmHg<br>n$_D^{20}$ = 1.4788 | rich amber, woody and flowery side notes; powerful, tenacious. |

*using the acetal CH$_3$CH(OEt)$_2$ of the carbonyl compound II

EXAMPLE 3

A. Perfume concentrate (tobacco)

| | parts per weight |
|---|---|
| lemon oil furocoumarin-free | 90 |
| bergamot oil furocoumarin-free | 200 |
| lavandin oil | 80 |
| juniper berries-essence | 20 |
| geranium oil Bourbon | 20 |
| cinnamon oil | 25 |
| linalyl acetate | 50 |
| rosmarin oil | 30 |
| linalool | 15 |
| phenylethyl dimethyl-carbinyl acetate | 50 |
| Rose base substitute | 10 |
| isobornyl acetate | 20 |
| methyl n-nonylacetaldehyde | 10 |
| styrallyl acetate | 10 |
| citronellol | 15 |
| 12-oxahexadecanolide | 10 |
| coumarin | 30 |
| Kephalis ® [4-(1-ethoxy-vinyl)-3,3,5,5-tetramethyl-cyclohexanone and its ethyl enol ether) | 15 |
| cedryl acetate | 20 |
| Lilial ® (p-tert. butyl-α-methyl-hydrocinnamic aldehyde | 15 |
| Irisantheme ® (mixture of methyl-ionones) | 25 |
| sandalwood oil East Indian | 20 |
| acetyl cedrene | 30 |
| oak moss absolute | 20 |
| Musk ketone (2,6-dinitro-3,5-dimethyl-4-acetyl-tertiary-butylbenzene) | 40 |
| patchouli oil | 10 |
| compound I', R=R$^1$=CH$_3$ | 30 |
| diethyl phthalate | 50 |
| 1,1-dimethyl isohexanol | 40 |
| | 1000 |

B. Concentrate for soaps (Fougere)

| | parts per weight |
|---|---|
| styrallyl acetate | 10 |
| bergamot oil substitute | 200 |
| benzyl acetate | 50 |
| Argeolene ® | 30 |
| patchouli oil substitute | 30 |
| cedarwood oil American | 30 |
| vetiver oil substitute | 20 |
| oak moss resinoid | 40 |
| musk ketone | 40 |
| benzyl salicylate | 50 |
| coumarin | 80 |
| geranium oil substitute | 100 |
| Sandela ® (3-isocamphyl-(5)-cyclohexanol) | 100 |
| compound I', R=H; R$^1$=C$_2$H$_5$ | 20 |
| Kephalis ® | 50 |
| diethyl phthalate | 150 |
| | 1000 |

C. Concentrate for foam bath (lemon)

| | parts per weight |
|---|---|
| bergamot oil substitute | 150 |
| lemon oil substitute | 340 |
| C$_{12}$—aldehyde (MNA) | 30 |
| petitgrain oil substitute | 40 |
| musk ketone | 70 |
| orange oil Brazil dest. | 200 |
| mandarin oil substitute | 100 |
| geranonitrile | 30 |
| 2,2,6-trimethyl-6-vinyltetrahydrofuran | 30 |
| compound I', R=H; R$^1$=CH$_3$ | 10 |
| | 1000 |

I claim:

1. A compound of the general formula

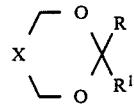

wherein R and R$^1$ are H, CH$_3$, C$_2$H$_5$, C$_3$H$_7$ or CH(CH$_3$)$_2$ and the sum of the carbon atoms in R and R$^1$ does not exceed 6, and X is caran-yliden (2,2) or caran-yliden (4,4).

2. A compound according to claim 1, which is 2,2,3',7',7'-pentamethyl-spiro[1,3-dioxane-5,2'-norcaran].

3. A compound according to claim 1, which is 2,3',7',7'-tetramethyl-spiro[1,3-dioxane-5,2'-norcaran].

4. A compound according to claim 1, which is 3',7',7'-trimethyl-2-ethyl-spiro[1,3-dioxane-5,2'-norcaran].

5. A compound according to claim 1, which is 2,3',7',7'-tetramethyl-2-ethyl-spiro[1,3-dioxane-5,2'-norcaran].

6. A compound according to claim 1, which is 3',7',7'-trimethyl-2,2-diethyl-spiro[1,3-dioxane-5,2'-norcaran].

7. A compound according to claim 1, which is 3',7',7'-trimethyl-spiro[1,3-dioxane-5,2'-norcaran].

8. An odorant composition containing a compound of the general formula

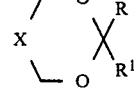

wherein R and R$^1$ are H, CH$_3$, C$_2$H$_5$, C$_3$H$_7$ or CH(CH$_3$)$_2$ and the sum of the carbon atoms in R and R$^1$ does not exceed 6, and X is caran-yliden (2,2) or caran-yliden (4,4).

* * * * *